United States Patent [19]
Sherman

[11] Patent Number: 5,921,996
[45] Date of Patent: Jul. 13, 1999

[54] SURGICAL CLAMP APPLIER/REMOVER AND DETACHABLE CLAMP

[75] Inventor: Benjamin Sherman, Milpitas, Calif.

[73] Assignee: Cardio Thoracic Systems, Inc., Cupertino, Calif.

[21] Appl. No.: 08/850,806

[22] Filed: May 2, 1997

[51] Int. Cl.[6] .................................................. A61B 17/28
[52] U.S. Cl. ........................................................... 606/157
[58] Field of Search ................................... 606/120, 138, 606/139, 142, 143, 151, 157, 158

[56] References Cited

U.S. PATENT DOCUMENTS

| | | | |
|---|---|---|---|
| 4,487,205 | 12/1984 | Di Giovanni et al. | 606/142 |
| 4,706,668 | 11/1987 | Backer | 606/142 |
| 4,944,741 | 7/1990 | Hasson . | |
| 4,979,937 | 12/1990 | Khorasani . | |
| 5,002,552 | 3/1991 | Casey | 606/157 |
| 5,133,724 | 7/1992 | Wilson, Jr. et al. . | |
| 5,201,746 | 4/1993 | Shichman . | |
| 5,242,456 | 9/1993 | Nash et al. . | |
| 5,250,056 | 10/1993 | Hasson . | |
| 5,275,614 | 1/1994 | Haber et al. . | |
| 5,282,806 | 2/1994 | Haber et al. . | |
| 5,282,812 | 2/1994 | Suarez, Jr. . | |
| 5,304,183 | 4/1994 | Gourlay et al. . | |
| 5,304,187 | 4/1994 | Green et al. . | |
| 5,368,600 | 11/1994 | Failla et al. . | |
| 5,415,666 | 5/1995 | Gourlay et al. . | |
| 5,423,809 | 6/1995 | Klicek . | |
| 5,425,705 | 6/1995 | Evard et al. . | |
| 5,428,039 | 6/1995 | Cohen . | |
| 5,447,515 | 9/1995 | Robicsek . | |
| 5,449,365 | 9/1995 | Green et al. | 606/142 |
| 5,452,733 | 9/1995 | Sterman et al. . | |
| 5,496,333 | 3/1996 | Sackier et al. . | |
| 5,498,998 | 3/1996 | Gehrke et al. . | |
| 5,501,698 | 3/1996 | Roth et al. . | |
| 5,536,251 | 7/1996 | Evard et al. . | |
| 5,569,274 | 10/1996 | Rapacki et al. . | |
| 5,571,121 | 11/1996 | Heifetz . | |
| 5,613,977 | 3/1997 | Weber et al. . | |
| 5,618,307 | 4/1997 | Donlon et al. . | |
| 5,626,607 | 5/1997 | Malecki et al. . | |

Primary Examiner—Michael Buiz
Assistant Examiner—William Lewis
Attorney, Agent, or Firm—Lyon & Lyon LLP

[57] ABSTRACT

A surgical clamp applier and a detachable clamp for temporarily occluding a vessel are disclosed. The clamp applier is designed to allow a surgeon to place and remove the clamp using only one hand. The clamp applier has a dial, a button, and a pulley actuator all accessible on the handle of the applier. The dial is used to lock the clamp onto the applier and to remove the clamp from the applier. The button is used to allow the pulley actuator to be used to manipulate the lower jaw of the clamp with respect to the upper jaw of the clamp, thus varying the amount of pressure exerted by the clamp on the vessel. The pulley actuator actuates a pulley system which engages the clamp, thereby manipulating the lower jaw of the clamp with respect to the upper jaw in a scissors-like manner, allowing the surgeon to properly clamp the target vessel. Various shapes and sizes of clamps are used for various procedures, but the clamps are all compatible with the clamp applier.

19 Claims, 12 Drawing Sheets

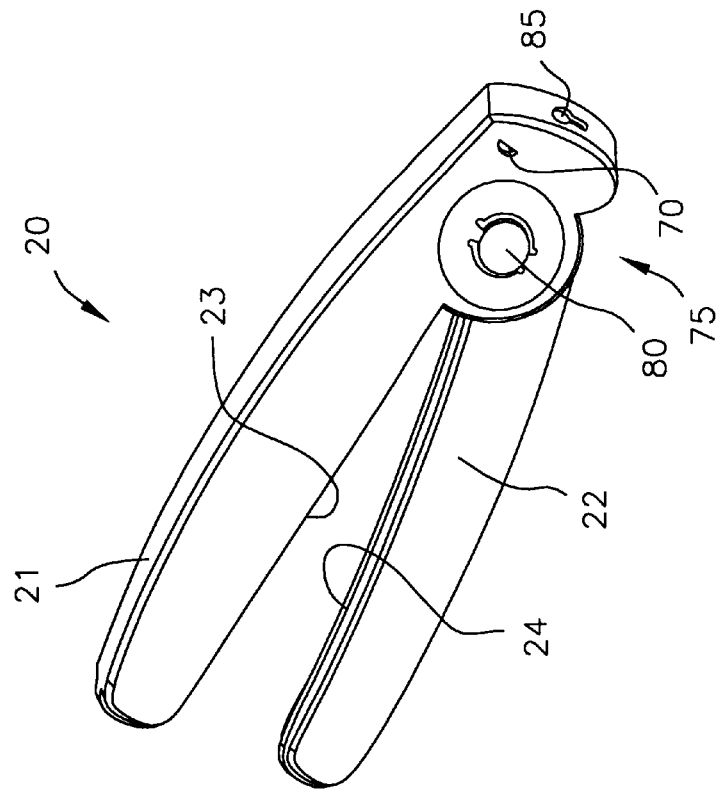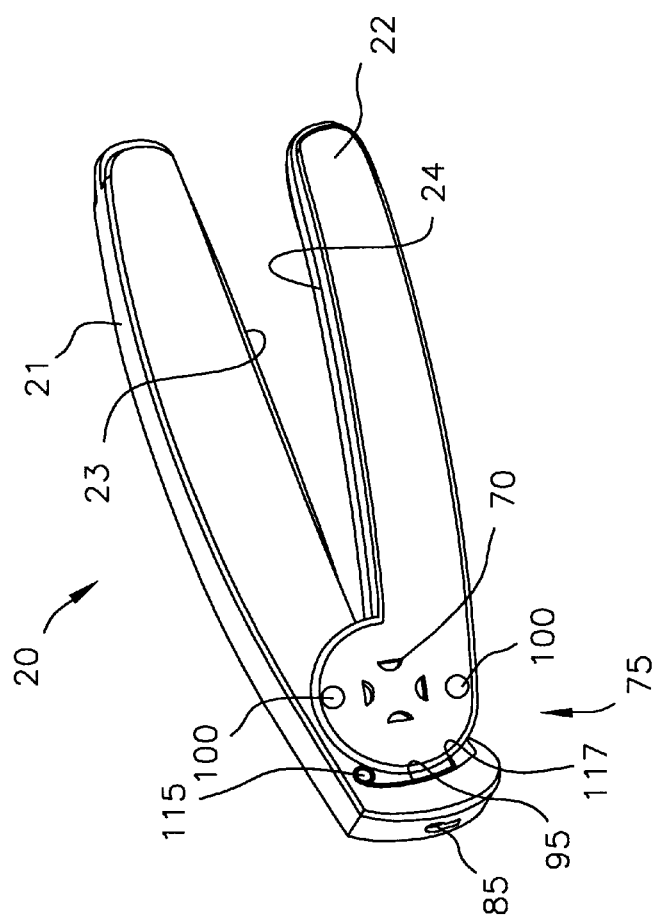
FIG. 2a

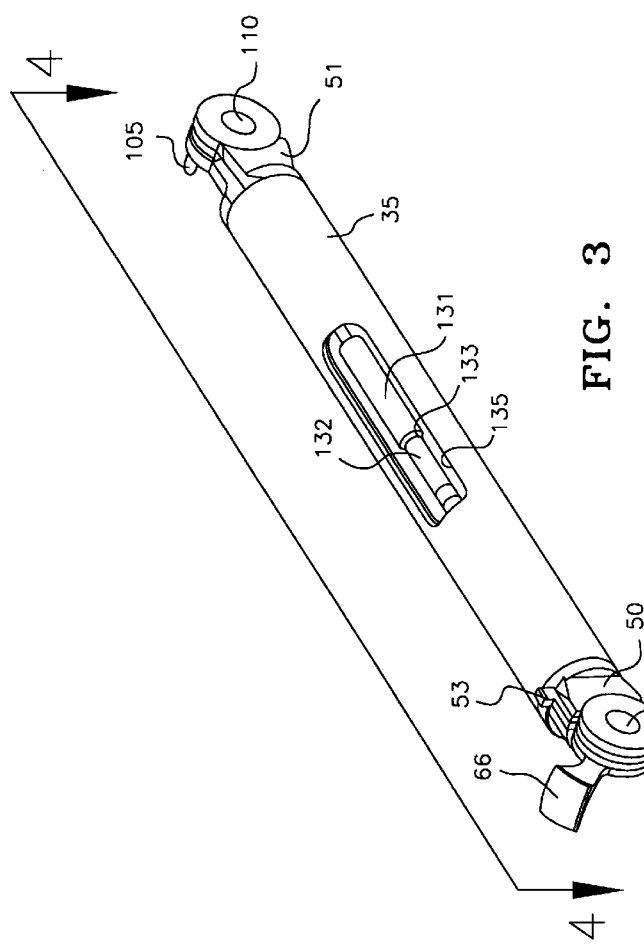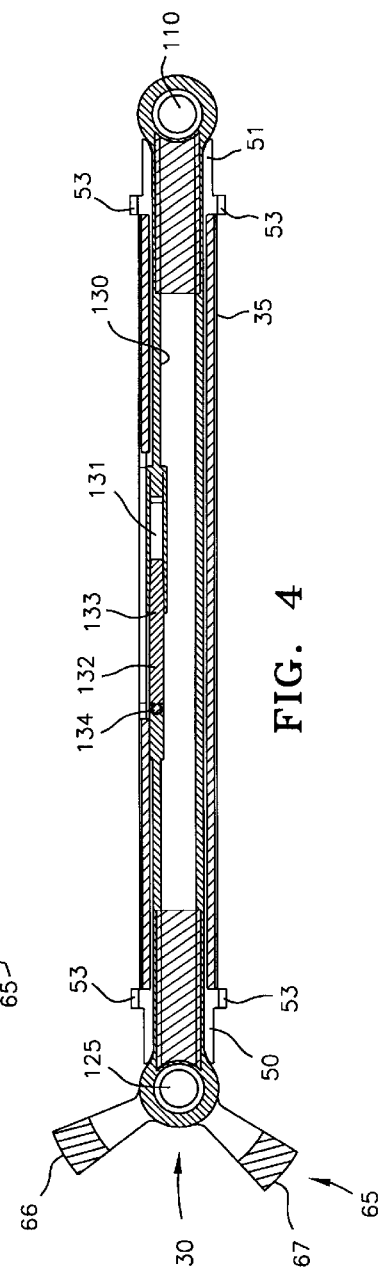

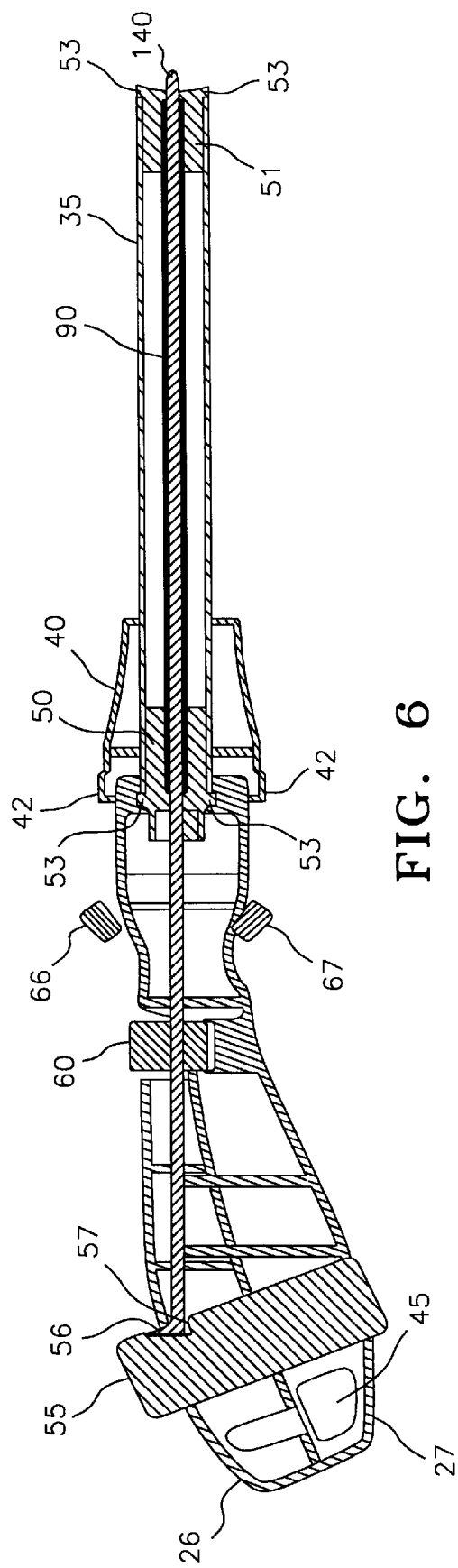
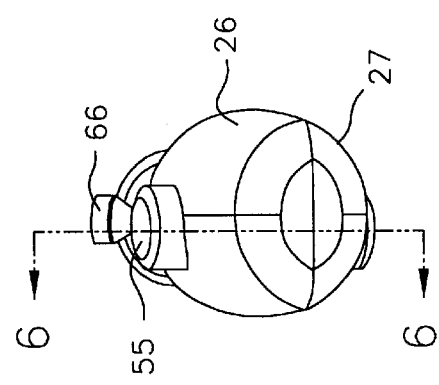
FIG. 6
FIG. 5

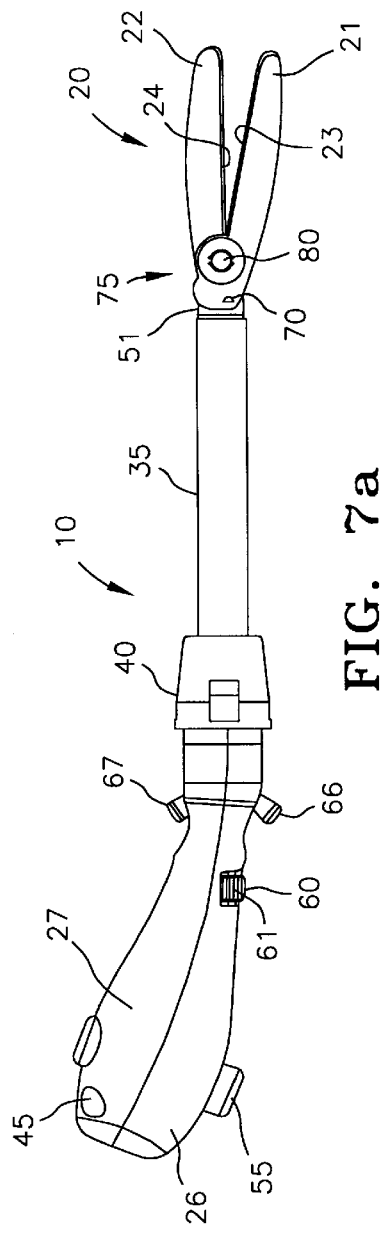
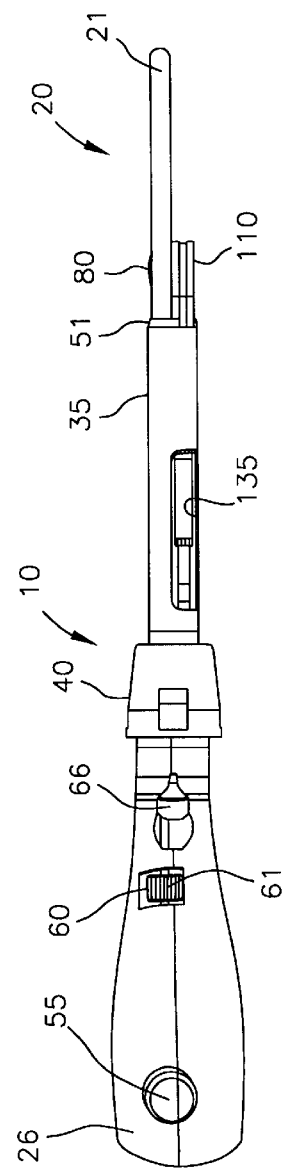
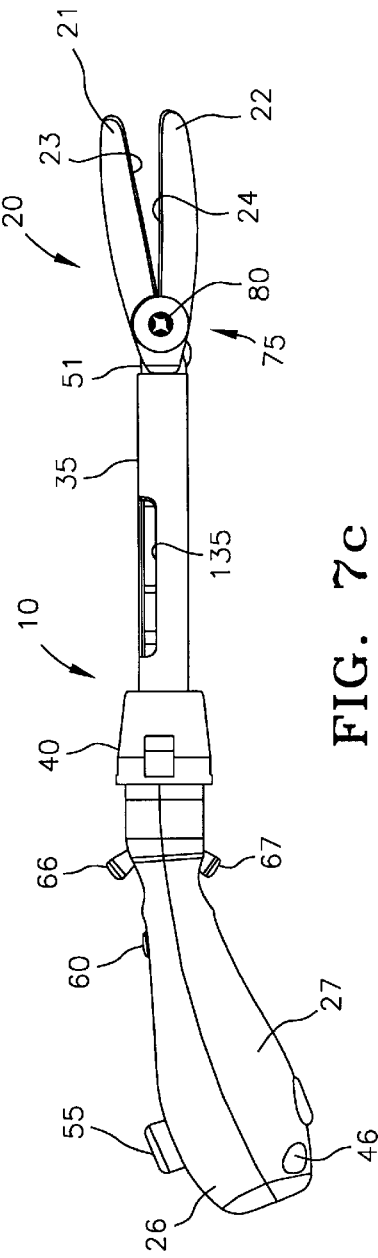
FIG. 7a
FIG. 7b
FIG. 7c

SURGICAL CLAMP APPLIER/REMOVER AND DETACHABLE CLAMP

FIELD OF THE INVENTION

The present invention relates generally to surgical instruments for occluding blood vessels during surgery, and more specifically to surgical clamps and clamp appliers.

BACKGROUND OF THE INVENTION

During surgery, it is often necessary to temporarily occlude blood flow through certain vessels to prevent leakage of blood through incisions made distal to the surgical site. Various devices and techniques exist for accomplishing temporary occlusion, including application of external surgical clamps to the vessels to be occluded. External surgical clamps are available in many shapes and sizes, with varying characteristics. Prior art clamps exist which are connected to elongated arms controlled by handles, such that a surgeon can apply and remove the clamp from outside the operating site. See for example U.S. Pat. No. 5,133,724 to Wilson, Jr. et. al, and U.S. Pat. No. 5,447,515 to Robicsek. A drawback of these clamps, however, is that once they are applied, the arms and handles remain in place and may hinder the surgeon's access to the operating site. Other clamp and clamp appliers exist which allow the surgeon to apply the clamp and then withdraw the clamp applier. See for example U.S. Pat. No. 5,282,812 to Suarez, Jr. But once these clamps are applied, if the surgeon opts to loosen the clamp he or she must determine and apply the appropriate amount of force by hand. Still other clamps and clamp appliers designed for tissue manipulation exist that utilize tethers for retracting tissue from an operating site. See for example U.S. Pat. No. 5,304,183 to Gourlay et. al. This system, however, requires the use of more than one instrument and therefore may require multiple entries into the operating subject, and may also result in multiple instruments potentially obstructing the surgeon's access and or view to the operating site.

With the advent of endoscopic surgery, devices have been designed to allow a surgeon to apply a clamp through a trocar sleeve, then remove the clamp applier from the trocar sleeve to make the trocar available for introducing other surgical instruments or clamps. See for example U.S. Pat. No. 5,368,600 to Failla et. al, and U.S. Pat. No. 5,569,274 to Rapacki et. al. A primary feature of the Failla invention is the ability of the surgeon to steer the clamp to the desired location by means at the proximal end of the applier. A primary feature of the Rapacki invention is the fact that the clamp is held by the applier at a single engagement point. Both of these inventions appear to solve the problem of having access obstructed by the applier; however, they both require the surgeon to use two hands to effectively manipulate the clamp. Furthermore, the clamps disclosed in the Failla and Rapacki patents exert a predetermined amount of pressure on the clamped vessel based on the natural biasing of the jaws of the clamps.

SUMMARY OF THE INVENTION

An object of this invention is to provide an improved method and device for clamping blood vessels during surgery.

Another object is to provide a surgical clamp for temporarily occluding blood flow through a vessel, and a clamp applier to apply the clamp and then be removed so as not to hinder the surgeon's access to the operating site.

Another object is to provide a surgical clamp for temporarily occluding blood flow through a vessel, and a clamp applier, which allow a surgeon to decrease the amount of pressure applied by the clamp without having to use any hand pressure.

Another object is to provide a surgical clamp for temporarily occluding blood flow through a vessel, and a clamp applier, which allow a surgeon to vary the amount of pressure applied by the clamp until the surgeon is satisfied the amount of pressure is proper.

Another object is to provide a surgical clamp for temporarily occluding blood flow through a vessel, and a clamp applier, which allow a surgeon to apply and manipulate the clamp with the use of only the clamp applier, and no other instruments.

Another object is to provide a surgical clamp for temporarily occluding blood flow through a vessel, and a clamp applier, which allow a surgeon to apply and manipulate the clamp with the use of only one hand, thus keeping the other hand free.

Another object is to provide a set of surgical clamps for temporarily occluding blood flow through various vessels, and a clamp applier, where the various clamps are all compatible with the clamp applier.

In a preferred embodiment of this invention, the above objects are accomplished by an ergonomic surgical clamp applier and a compatible corresponding clamp which allow a surgeon to apply and remove the clamp using only one hand. The clamp applier has a dial, a button, and a pulley actuator all accessible on the handle of the applier. The dial is used to lock the clamp onto the applier and to remove the clamp from the applier by manipulating a conduit into and out of a keyhole in the clamp. The button is used to allow the pulley actuator to be used to manipulate the lower jaw of the clamp with respect to the upper jaw of the clamp, thus varying the amount of pressure exerted by the clamp on the vessel.

The clamp is designed to be disposed after a single use, and clamps of various shapes and sizes are contemplated for occlusion of various vessels during various types of surgery. It is important, however, that the clamps have a required keyhole, pulley-pin holes, and jaw-locking mechanism, as will be described in the detailed description, to be compatible with the clamp applier.

The clamp applier and clamp may be configured for application in minimally invasive surgeries using cannulae or small incisions in the chest wall, as well as for conventional surgical techniques such as a median sternotomy (cutting the sternum longitudinally) or a lateral thoracotomy (cutting between two ribs).

Other advantages of this invention will become apparent from the detailed description of preferred embodiments which follow.

BRIEF DESCRIPTION OF THE DRAWINGS

FIG. 2a shows perspective views of both sides of the clamp in FIG. 1.

FIG. 3 is a perspective view of the tube and pulley system of the present invention.

FIG. 4 is a cross-section along line 4—4 of FIG. 3, showing the tube and pulley system of the present invention.

FIG. 5 is a perspective view of the proximal end of the clamp applier, along the longitudinal axis of the clamp applier.

FIG. 6 is a cross section along line 6—6 of FIG. 5, of the clamp applier.

FIG. 7a is a side plan view of the surgical clamp applier with the clamp of FIG. 2a attached, showing one side of the clamp.

FIG. 7b is a top plan view of the surgical clamp applier with the clamp of FIG. 2a attached.

FIG. 7c is a side plan view of the surgical clamp applier with the clamp of FIG. 2a attached, showing the side of the clamp not shown in FIG. 7a.

DETAILED DESCRIPTION

Figure 1:
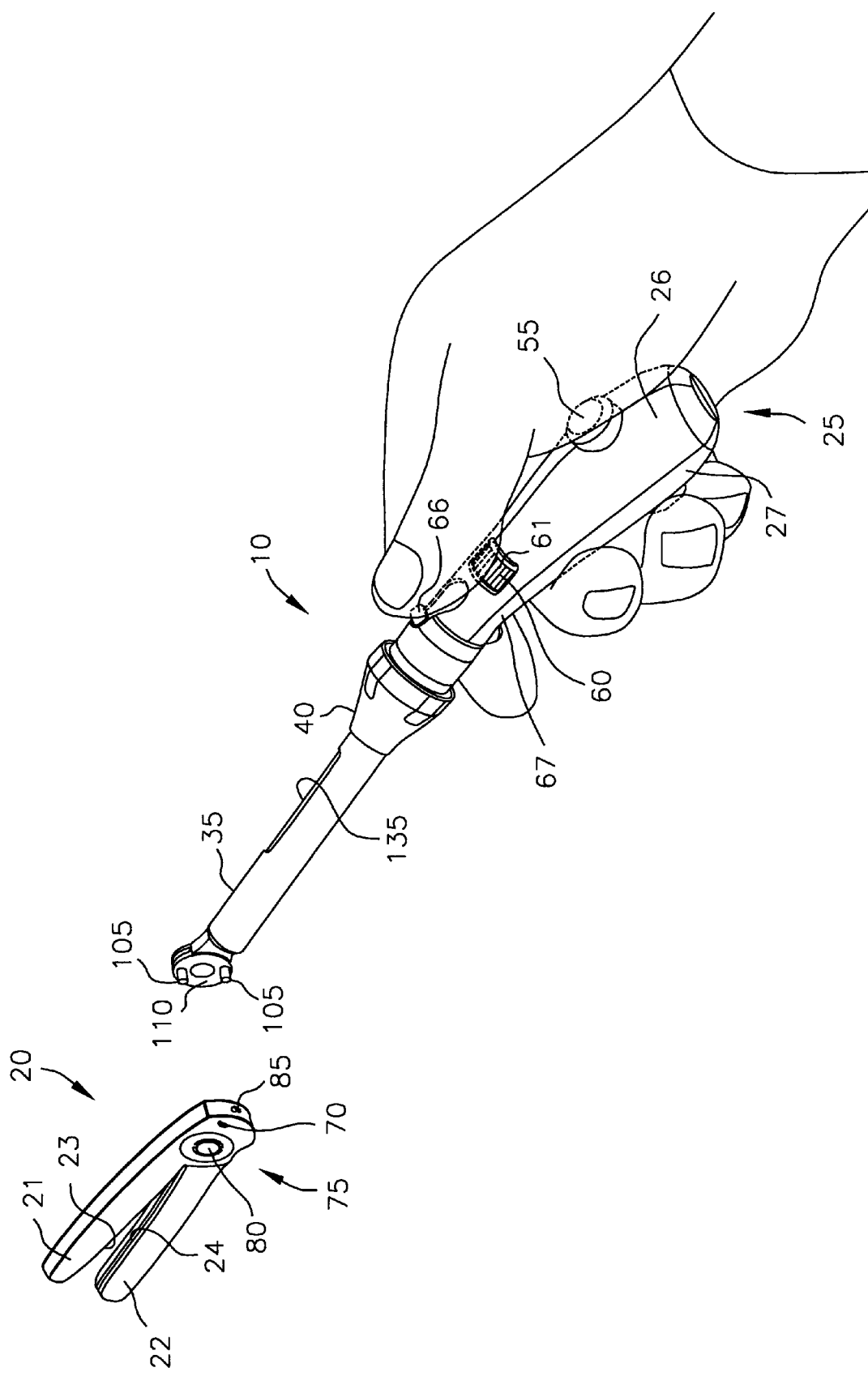
FIG. 1 is a perspective view of the surgical clamp applier and a first embodiment of the detachable clamp of the present invention, showing a surgeon's hand gripping the clamp applier in a preferred position, and showing the clamp oriented such that it is ready to be attached to the clamp applier.

FIG. 1 shows a surgical clamp applier 10 and detachable clamp 20 of the present invention, with a surgeon's hand gripping the clamp applier 10 in a preferred position, and the clamp 20 oriented such that it is ready to be attached to the clamp applier 10 as will be described in more detail shortly and as is seen in FIG. 7a, FIG. 7b, and FIG. 7c. The clamp applier 10 includes a two-piece handle 25 and a pulley system 30 housed in a tube 35 (FIG. 3 and FIG. 4). A connector 40 is adapted to help secure the tube 35 in proper alignment with respect to the handle 25, as well as to secure the two pieces of the handle 25 to each other. This is accomplished by small prongs 42 extending radially inward from the proximal end of the connector 40 which engage corresponding grooves molded into the handle 25 as best seen in FIG. 6. In addition, the distal end of the connector 40 frictionally engages the outer surface of the tube 35.

The handle 25 comprises an upper portion 26 and a lower portion 27. The upper portion 26 is secured to the lower portion 27 at the proximal end of the handle 25 by two screws (not shown) which are housed in screw cavities 45 and 46 (FIG. 6, FIG. 7a, and FIG. 7c). At the distal end of the handle 25, the upper portion 26 and lower portion 27 are held in place by the connector 40 which squeezes them against a proximal pulley retainer 50, as is best seen in FIG. 6. The handle 25 is designed to comfortably fit in one hand of a surgeon such that the surgeon can use the one hand to manipulate the clamp 20 as desired. Thus, the handle 25 is angled slightly downward proximally to fit the natural curve of the surgeon's hand. This is best seen in FIG. 1. A button 55, a dial 60, and a pulley actuator 65 are all accessible through openings in the handle 25 and are within reach of the surgeon's one hand. The button 55, dial 60, and pulley actuator 65 are used in conjunction with each other to lock or release the clamp 20 onto or off of the clamp applier 10, and to manipulate the lower jaw 22 of the clamp 20 in a scissors-like manner with respect to the upper jaw 21 of the clamp 20. These components of the invention will first be described independently, but it is important to understand that they all work together to effect overall operation of the clamp applier 10 and clamp 20.

Turning now to FIGS. 2a–2f, multiple embodiments of the clamp 20 are shown. The various embodiments illustrate various shapes and sizes of the clamps 20 for use in various procedures, and therefore the clamps 20 have some varying characteristics. But the clamps 20 also have many similar characteristics, and like parts will be referred to by like reference numbers in the drawings. Differences will be pointed out where appropriate. Also, though the detailed description of the clamps 20 to follow will necessarily refer to cooperating components of the clamp applier 10, such cooperating components will be described in detail subsequently in conjunction with the description of FIGS. 3–8.

The clamps 20 are preferably made from two pieces of injection-molded plastic. The injection molding results in indentations 70 due to nodules in the mold which allow the molded pieces to be removed. The two pieces constitute an upper jaw 21 and a corresponding lower jaw 22, each having tissue-contacting surfaces 23 and 24 respectively which engage the tissue being clamped when the clamp 20 is in use (see FIGS. 2b, 2d, 2f, and 2h). The surfaces 23 and 24 are preferably made of a soft compressible material such as foam rubber or silicone to minimize trauma to the tissue contacted. The jaws 21 and 22 are connected to each other at a joint 75, which the present invention contemplates as a conventional pivot assembly 80. It will be understood by those skilled in the art, however, that other forms of joints may be used without departing from the present invention.

Figure 9:
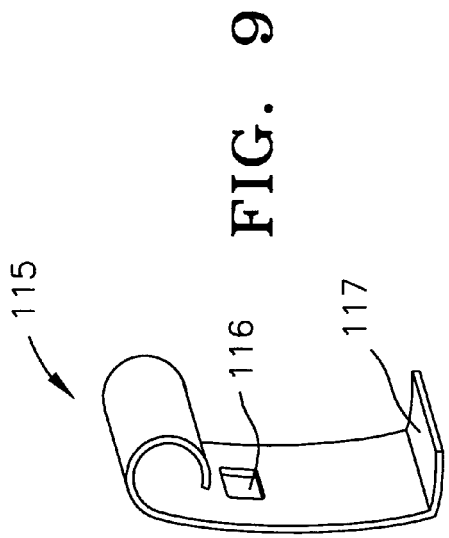
FIG. 9 shows the jaw-locking mechanism, a leaf spring, used in the joint of the clamp of the present invention.

At the proximal end of the joint 75, there is a keyhole 85 in the upper jaw 21 adapted to receive a key-like tip 91 (FIG. 8) of a conduit 90 from the tube 35. The key-like tip 91 is used to secure the clamp 20 onto the clamp applier 10, by catching onto a recess 95 molded into the inside of the upper jaw 21 at the joint 75. Also, on the side of the lower jaw 22 opposite the pivot assembly 80, there are two pulley-pin holes 100 (FIG. 2a) for receiving pins 105 from a distal pulley 110. The pulley-pin holes 100 receive the pins 105 to allow the surgeon to manipulate the lower jaw 22 of the clamp 20 in a scissors like fashion with respect to the upper jaw 21, once the clamp 20 is locked onto the clamp applier 10. A preferred jaw-locking mechanism is a leaf spring 115 (FIG. 2a and FIG. 9), which is secured to the inside of the joint 75 by a small protrusion (not shown) molded into the upper jaw 21 which extends through a slot 116 in the leaf spring 115. A horizontal tooth 117 at the bottom of the leaf spring 115 angles slightly upward, and engages corresponding horizontal ridges (not shown) molded into the lower jaw 22 to prevent the lower jaw 22 from opening. When the leaf spring 115 is buckled, however, as will be described shortly, the tooth 117 no longer engages the ridges and the lower jaw 22 is therefore free to be adjusted.

As previously stated, the clamps may vary in size as required for various procedures. However, for the purpose of illustration, the average dimensions of a first embodiment of the clamp 20, shown in FIG. 2a and FIG. 2b, will be discussed. When fully closed, the distance from the proximal end to the distal end is approximately between 2.0 to 10.0 centimeters, 10.0 centimeters being sufficient to clamp both the aorta and pulmonary vein if desirable. The distance from the top of the upper jaw 21 to the bottom of the lower jaw 22 is approximately between 2.0 to 2.5 centimeters, and the distance from the proximal end of the clamp 20 to the center of the pivot assembly 80 is approximately 1.0 to 1.3 centimeters. Additionally, the thickness of each of the jaws 21 and 22 of the clamp 20 in FIG. 2a is approximately 0.50 centimeters.

Figure 2B:
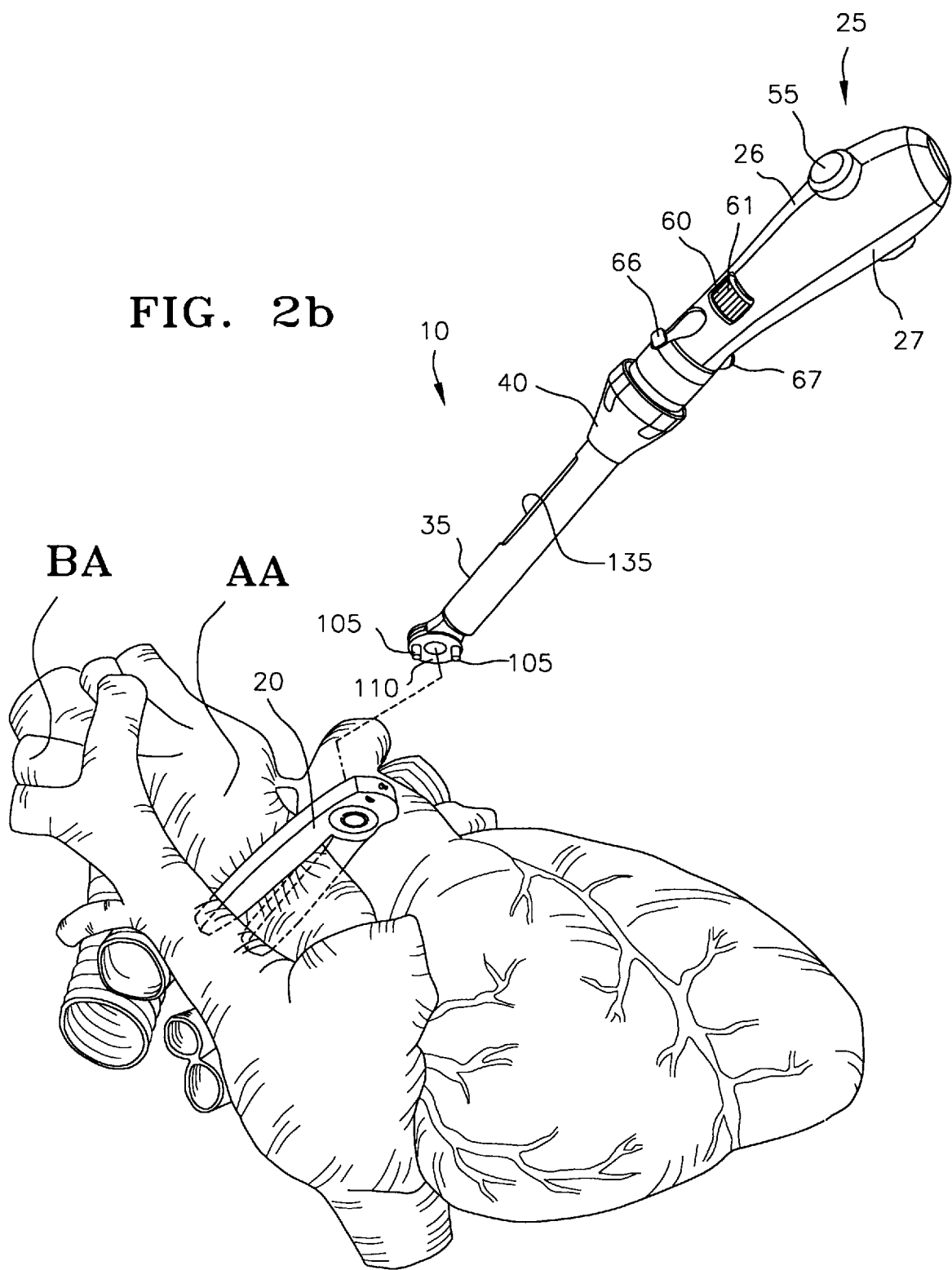
FIG. 2b shows the clamp of FIG. 2a in use externally cross-clamping the aorta.

The clamp 20 in FIG. 2a may be used on various vessels, and is shown in FIG. 2b being used to externally cross-clamp the ascending aorta AA downstream of the coronary ostia (not shown) and upstream of the brachiocephalic artery BA. Such cross-clamping of the ascending aorta is provided to isolate the heart and coronary vessels from the circulatory system during cardiopulmonary bypass (CPB). Aortic cross-clamping is commonly used for various cardiac procedures including valve repair and replacement, coronary artery bypass grafting, septal defect repair, heart transplantation, and any procedure requiring CPB or the temporary occlusion of a target vessel.

Figure 2C:
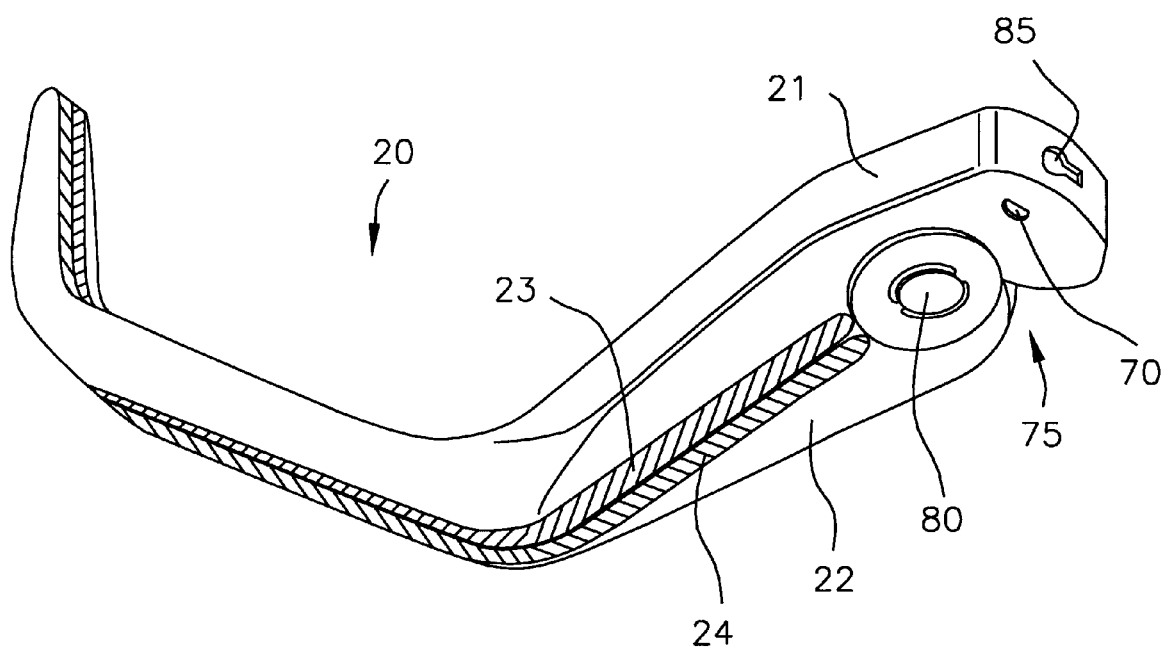
FIG. 2c is a perspective view of a second embodiment of the detachable clamp of the present invention, known as a side-biting clamp.
Figure 2D:
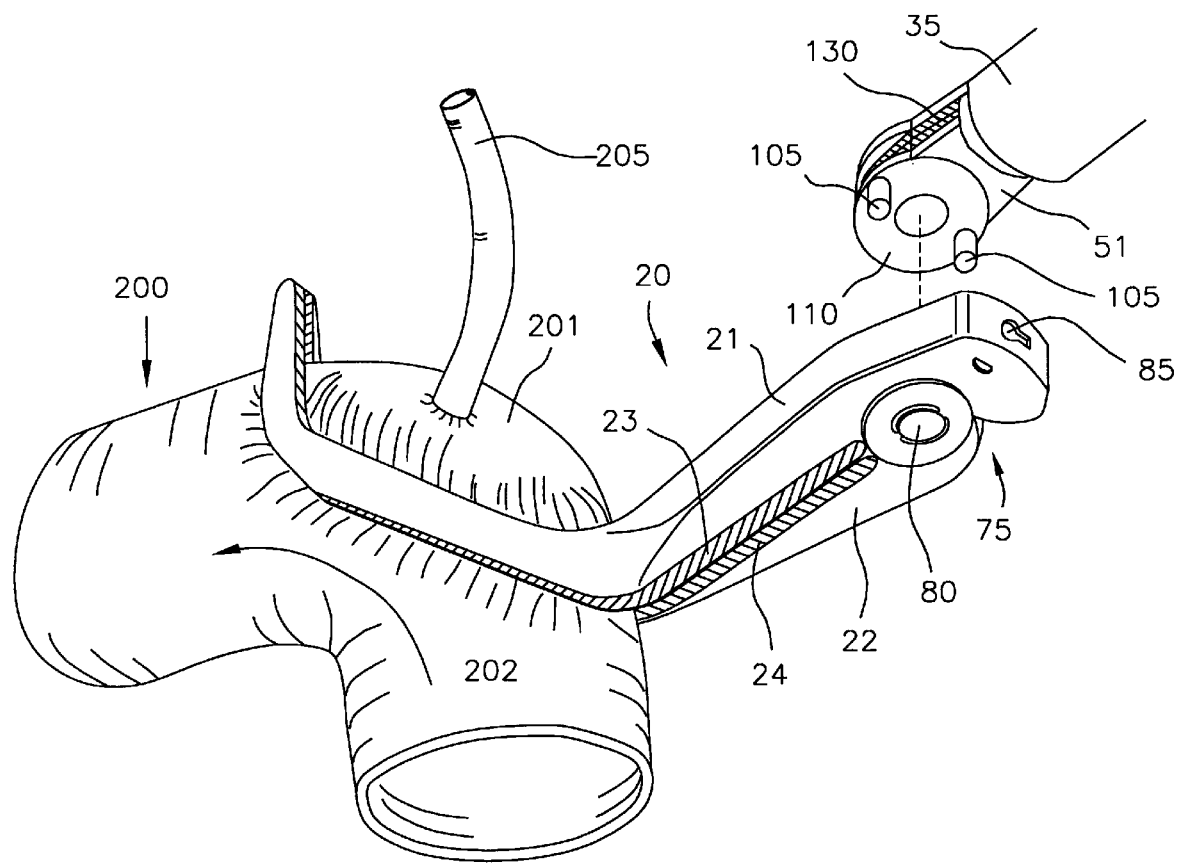
FIG. 2d shows the clamp in FIG. 2c in use isolating an area of a vessel to be operated upon.

Turning now to FIG. 2c and FIG. 2d, a second embodiment of the clamp 20, often referred to as a side-biting clamp, is used to isolate a portion 201 of a vessel 200 and completely block off blood flow through the isolated portion 201 of the vessel 200, while allowing blood to flow through the remaining portion of the vessel 200 as indicated by arrow 202. This configuration is suitable for isolating an area of the aorta, for example, to which the proximal end of a bypass vessel 205 is anastomosed to the aorta in a coronary artery bypass graft procedure. Additionally, such a clamp configuration is suitable when only partial occlusion of the vessel is desired. For example, during a mitral valve repair procedure in a patient whose aortic valve is working sufficiently to continue pumping blood during the procedure, it may be desirable to partially occlude the aorta.

Figure 2E:
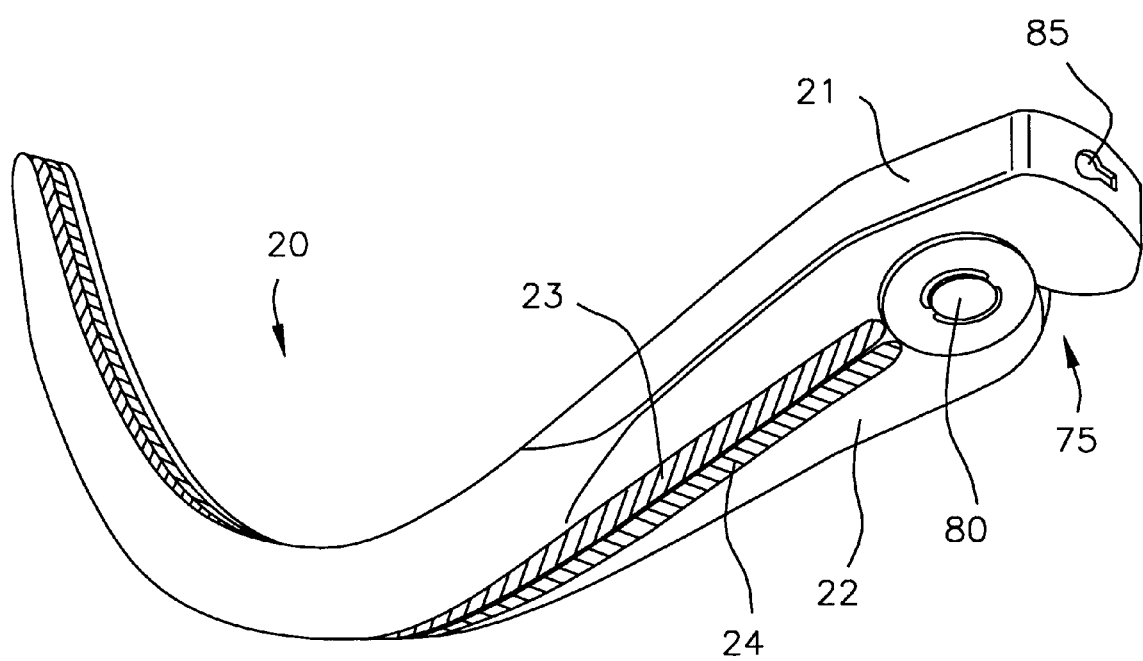
FIG. 2e is a perspective view of a third embodiment of the detachable clamp of the present invention, having curved jaws.
Figure 2F:
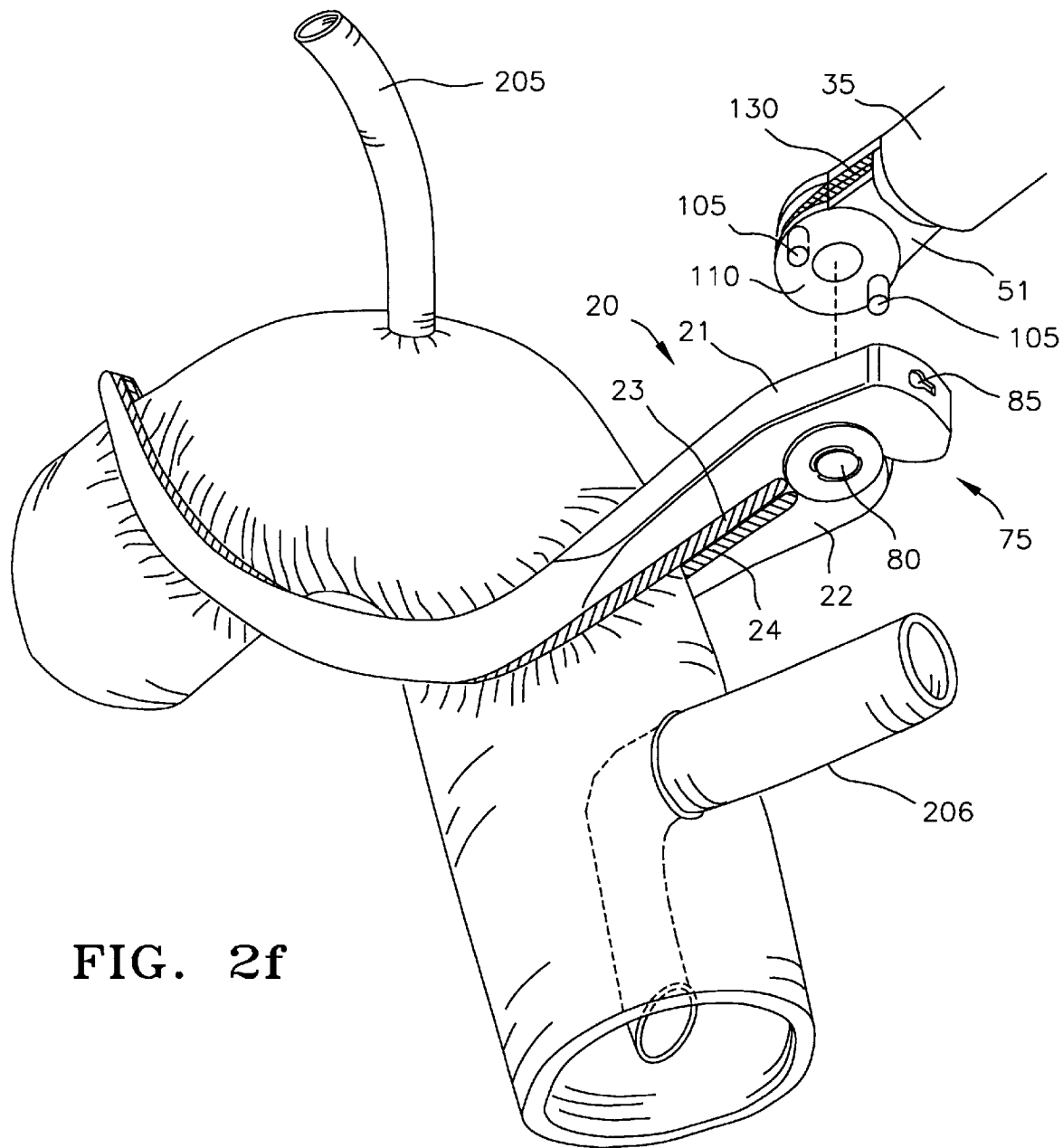
FIG. 2f shows the clamp in FIG. 2e in use isolating an area of a vessel to be operated upon.
Figure 2H:
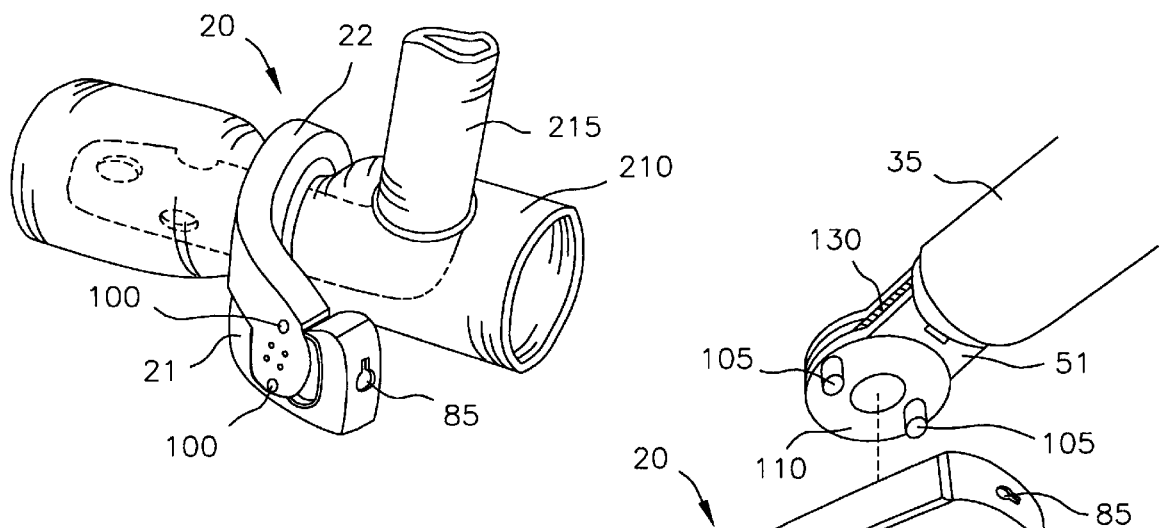
FIG. 2h shows the clamp in FIG. 2g in use sealing the lumen of a vessel about the exterior of a cannula.
Figure 2G:
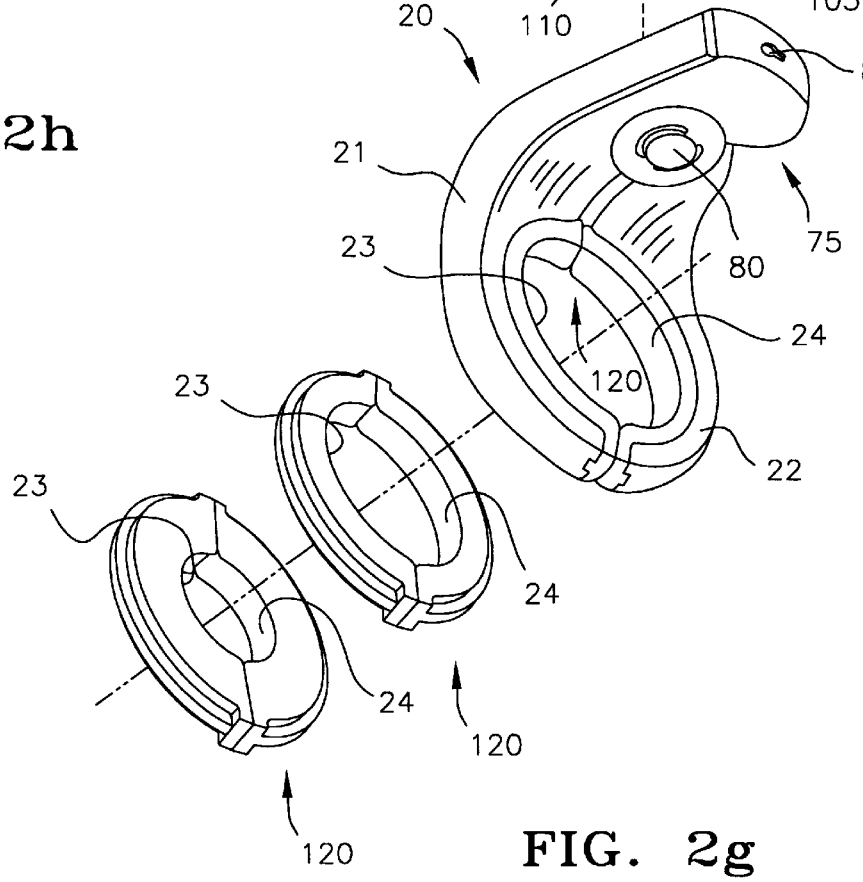
FIG. 2g is a perspective view showing various sizes of a fourth embodiment of the detachable clamp of the present invention, having substantially C-shaped jaws which form an annular configuration when in a closed position.
Figure 8:
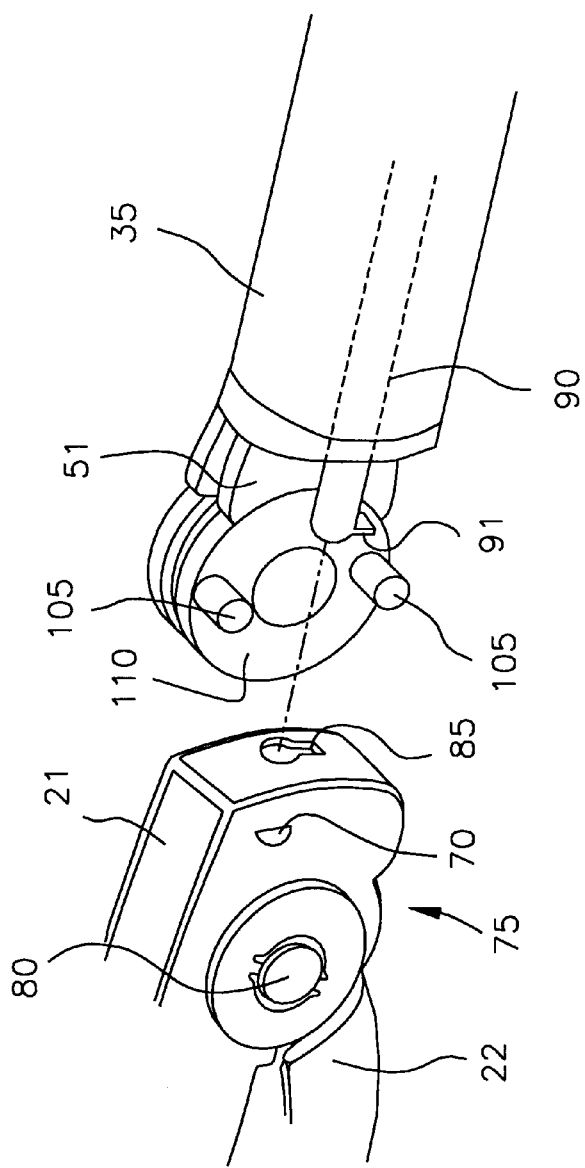
FIG. 8 shows the key-like tip of the conduit extending from the clamp applier towards a keyhole in the proximal end of a clamp.

Turning now to FIG. 2e and FIG. 2f, a third embodiment of the clamp 20 is shown having curved jaws. Such a configuration is helpful, for example, for cross-clamping a diseased aorta having internal calcification. Direct clamping is undesirable in such a situation because plaque deposits may break loose from the inner wall of the aorta. The clamp 20 allows the entire width of the aorta to be cross-clamped, yet provides an open space for anastomosing a graft vessel 205, while avoiding risky areas of calcification. FIG. 2f also shows a cannula 206 which may be used for arterial perfusion during CPB. Turning now to FIG. 2g and FIG. 2h, a fourth embodiment of the clamp 20 is shown having substantially C-shaped jaws which form an annular configuration when in a closed position. This configuration is suitable to atraumatically seal the lumen of a vessel 210, such as the vena cavae, about the exterior of a cannula 215, such as a venous drainage cannula for CPB.

The clamp in FIG. 2g is shown with detachable rings 120 which contain the tissue-contacting surfaces 23 and 24. The rings 120 have various radial thicknesses for use on various vessels, but the outside diameters of the rings 120 must be the same and the various rings must be similarly adapted to mate with the jaws 21 and 22 of the clamp 20. A ring 120 designed to clamp the inferior vena cava, for example, has an inner diameter of slightly less than 1.55 centimeters to 1.95 centimeters, which is a typical outer diameter of an inferior vena cava. Thus, the clamp 20 when closed could properly seal the lumen of the inferior vena cava about the exterior of a cannula 215. Similarly, a ring 120 designed to clamp the superior vena cava has an inner diameter of slightly less than 1.85 centimeters to 2.30 centimeters, which is a typical outer diameter of a superior vena cava.

To avoid the need for rings with various radial thicknesses, the tissue-contacting surfaces 23 and 24 may comprise inflatable elements coupled to a means for inflating and deflating the surfaces 23 and 24 to a produce a ring of desired diameter.

Though various embodiments of the clamp 20 have been described, it is important that the clamps 20 of the present invention have the required keyhole 85, pulley-pin holes 100, and leaf spring 115 jaw-locking mechanism as herein described, in order to be compatible with the clamp applier 10. Furthermore, the clamps 20 are used preferably for clamping major arteries such as the aorta, and major veins such as the vena cavae, but the clamps 20 are not limited thereto.

Turning now to FIG. 3 and FIG. 4, the pulley system 30 and tube 35 of the present invention are shown. The pulley system 30 includes a proximal pulley 125 and a distal pulley 110, with a continuous loop of cable 130 wrapped therearound. The pulleys 125 and 110 are preferably made of plastic, and are held in place by the cable 130 and by retainers 50 and 51 respectively which have prongs 53 to prevent the retainers 50 and 51 from collapsing back into the tube 35. The distal pulley 110 has two pins 105 (see FIG. 1) extending laterally therefrom by approximately 0.32 centimeters. The pins 105 fit into corresponding pulley-pin holes 100 at the proximal end of the clamp 20. When the pins 105 are engaged with the pulley-pin holes 100 and the clamp 20 is locked onto the clamp applier 10 as more fully described shortly, actuating the proximal pulley 125 causes the cable 130 to correspondingly actuate the distal pulley 110 such that the pins 105 manipulate the lower jaw 22 of the clamp up or down in a scissors-like fashion with respect to the upper jaw 21. Specifically, the pulley actuator 65 has an upper portion 66 and a lower portion 67. When the upper portion 66 is pulled toward the button 55 (e.g. with the tip of the surgeon's thumb as is best seen in FIG. 1) or the lower portion is pushed away from the button 55 (e.g. with the surgeon's index finger as is best seen in FIG. 1), then the top of the distal pulley 110 rotates toward the button 55 about an axis perpendicular to the longitudinal axis of the clamp applier 10, causing the lower jaw 22 of the clamp 20 to swing upward and thereby close the clamp 20. And when the upper portion 66 is pushed away from the button 55 or the lower portion is pulled toward the button 55, then the top of the distal pulley 110 rotates away from the button 55 about the same axis, causing the lower jaw 22 of the clamp 20 to swing downward and thereby open the clamp 20. The pulley actuator 65 preferably has a total range of movement of approximately ninety degrees.

The tube 35 is substantially cylindrical and encases the pulley system 30. A longitudinal opening 135 in the tube 35 allows access to the cable 130 so that the cable 130 may be connected together as described shortly to form a single continuous cable 130. The tube 35 also holds the pulley retainers 50 and 51 frictionally against the respective pulleys 125 and 110 such that the tension in the cable 130 is proper.

The cable is preferably woven stainless steel mesh, and approximately 0.9 to 1.0 millimeters in diameter. The cable 130 has a female member 131, preferably female-threaded, clamped on to one end, and a male member 132, preferably male-threaded, clamped on to the other end, as best seen in FIG. 4. The male end 132 is screwed into the female end 131 at location 133 to connect the two ends of the cable 130 and form a single continuous cable wrapped around the pulleys 125 and 110. This connection may be performed through the longitudinal opening 135 in the tube 35, where the cable 130 may also be slightly adjusted to increase or decrease the cable tension. There is a ball and socket joint 134 or other similar means at the non-male end of the male member 132, which allows the male member 132 to screw into or otherwise rotatably enter the female member 131 without causing the corresponding portion of the cable 130 to twist about itself.

Referring now to FIG. 6, a cross-section along line 6—6 of FIG. 5 is shown, of the assembled clamp applier 10. The button 55 has an angled notch 56 with a rim 57 that provides support for a rod 140. Likewise, the rod 140 prevents the button 55 from sliding out of the handle 25. The rod 140 passes through a tunnel in the dial 60, and through a conduit 90 which runs substantially the entire length of the tube 35. The rod 140 is frictionally engaged with the dial 60 and with the conduit 90 at all points of intersection. The conduit 90 has a key-like tip 91 (see FIG. 8) at its distal end which is shaped to fit into the keyhole 85 of the clamp 20 when properly aligned.

In preparation for applying the clamp 20 to a vessel, the clamp 20 must first be locked onto the clamp applier 10. This is done by first manually inserting the pins 105 on the distal pulley 110 into the corresponding pulley-pin holes 100 of the clamp 20. Next, the key-like tip 91 of the conduit 90 must be inserted into the keyhole 85 of the clamp 20 and locked thereto. This is done by pushing down the dial 60, which is rigidly fixed to the conduit 90, and then sliding the dial 60 distally (e.g. with the surgeon's thumb as is best seen in FIG. 1). Pushing down the dial 60 increases friction between the dial 60 and the conduit 90, and sliding the dial 60 distally then pushes the conduit 90 correspondingly distally. The conduit 90 is aligned with the button 55 which is slightly off-center of the longitudinal axis of the clamp applier 10, as is best seen in FIG. 5. The off-center alignment is necessary to align the key-like tip 91 of the conduit 90 with the keyhole 85 of the clamp 20. This is best seen in FIG. 7b when viewed in conjunction with FIG. 1, which figures show that the attached clamp 20 is locked onto the clamp applier 10 slightly off-center from the longitudinal axis of the clamp applier 10. Once the key-like tip 91 of the conduit is extended and inserted successfully into the keyhole 85, the dial 60 is rotated approximately one-quarter turn or ninety degrees counter-clockwise about the longitudinal axis of the clamp applier 10. This correspondingly rotates the conduit 90 one-quarter turn such that the key-like tip 91 catches against the recess 95 (FIG. 2a) molded into the upper jaw 21. The key-like tip 91 being caught onto the recess 95, in conjunction with the pins 105 being properly inserted into the corresponding pulley-pin holes 100, is sufficient to lock the clamp 20 onto the clamp applier. The dial 60, which has a plurality of ridges 61 on its surface to provide better traction, also remains slightly distal to its original position. The resulting configuration is shown in FIG. 7a, FIG. 7b, and FIG. 7c.

To apply the clamp 20 to a vessel as shown in FIGS. 2b, 2d, 2f, and 2h, the clamp 20 must be positioned near the vessel, and then opened sufficiently to surround the vessel. The positioning technique of the surgeon will depend on the type of surgery being performed, and the type of clamp 20 being used, as previously described in conjunction with FIGS. 2a–2h.

Once the clamp 20 is properly positioned, the surgeon must open the clamp 20 by lowering the lower jaw 22. Normally, the lower jaw 22 will rest at its previously set position, as the tooth 117 of the leaf spring 115 will be engaging the horizontal ridges (not shown) molded into the lower jaw 22 as previously described. To change the previously set position, the leaf spring 115 must be buckled to force the tooth 117 away from the ridges in the lower jaw 22. This is done by depressing the button 55 (e.g. with the ball of the surgeon's thumb as is best seen in FIG. 1). As previously described, and as seen in FIG. 6, this action forces the rod 140 distally to a distance sufficient to buckle the leaf spring 115. As long as the button 55 remains depressed, the leaf spring 115 remains buckled, and hence the lower jaw 22 may be freely manipulated using the pulley actuator 65. It is important to understand that the pulley actuator 65 is designed to be used only while the button 55 is also depressed.

Specifically, while the button 55 is depressed and the leaf spring 115 is therefore buckled, the pulley actuator 65 is slowly manipulated to cause a corresponding rotation of the distal pulley 110 as previously described. Due to the engagement of the pins 105 with the pulley-pin holes 100 in the clamp 20, the rotation of the distal pulley 110 causes the lower jaw 22 to correspondingly open or close, depending on the direction of movement of the actuator 65 as previously described. Once the clamp 20 is opened sufficiently wide enough to surround the vessel, and the clamp 20 is positioned around the vessel, the surgeon then adjusts the lower jaw 22 to a desired position such that the vessel is properly occluded. When satisfied, the surgeon then lifts the ball of his or her thumb off of the button 55 and uses his or her other fingers to push the button 55 from below up to its original position. This allows the rod 140 to retract distally, unbuckling the leaf spring 115 such that the leaf spring's 115 tooth 117 regains its grip on the lower jaw 22 of the clamp 20 and thus stabilizes the lower jaw's 22 position with respect to the upper jaw 21. If the surgeon determines that the grip is too tight, and must be loosened, he or she may depress the button 55 to again buckle the leaf spring 115, and then readjust the lower jaw 22 as previously described.

When the clamp 20 is properly adjusted, the surgeon then removes the clamp applier 10 from the clamp 20 to eliminate any possible obstruction the clamp applier 10 might otherwise cause. This is accomplished by first rotating the dial 60 approximately ninety degrees clockwise, thus removing the key-like tip 91 from the recess 95, and then sliding the dial 60 proximally to cause the key-like tip 91 to exit the keyhole 85. The clamp applier 10 is then moved slightly laterally away from the clamp 20 to remove the pins 105 from the pulley-pin holes 100 in the clamp 20, and the surgeon then withdraws the clamp applier 10 from the operating area. The clamp 20 then remains in position until the surgery is complete.

Once surgery is complete, the surgeon then removes the clamp 20 from the vessel. This is accomplished by first locking the clamp 20 onto the clamp applier 10 as previously described. Next, the leaf spring 115 is buckled and the lower jaw 22 is opened as previously described. The surgeon may then remove the clamp applier 10, with the clamp 20 attached, without traumatizing the previously occluded vessel.

While certain embodiments are illustrated in the drawings and have just been described herein, it will be apparent to those skilled in the art that many modifications can be made to the embodiments without departing from the inventive concepts described. Accordingly, the invention is not to be restricted except by the claims which follow.

What is claimed is:

1. A surgical clamp applier having a proximal end and a distal end, the clamp applier comprising:

a handle;

a pulley system comprising a proximal pulley, a distal pulley, and a cable formed into a loop and wrapped around the pulleys such that the cable frictionally engages at least part of the circumference of the proximal pulley and at least part of the circumference of the distal pulley, and when operative the cable prevents longitudinal movement of the pulleys away from each other, the distal pulley having a plurality of pins extending laterally therefrom;

a tube which houses substantially the entire loop of cable, the tube having a proximal end and a distal end;

a connector to connect the pulley system and the tube to the handle;

a pulley actuator at the proximal end of the clamp applier to actuate the pulley system;

a conduit extending substantially the entire length of the tube and secured substantially therein, the conduit having a distal end for releasably engaging a clamp;

a rod extending substantially the entire length of the handle and of the tube, and housed substantially therein, the rod passing through the conduit;

means at the proximal end of the clamp applier for propelling the rod distally; and means at the proximal end of the clamp applier for rotating the conduit about its longitudinal axis and for propelling the conduit distally.

2. The clamp applier as in claim 1 wherein the means for propelling the rod distally is a button.

3. The clamp applier as in claim 1 wherein the means for rotating the conduit about its longitudinal axis and for propelling the conduit distally is a dial.

4. The clamp applier as in claim 1 further comprising a proximal pulley retainer secured between the proximal end of the tube and the proximal pulley, and a distal pulley retainer secured between the distal end of the tube and the distal pulley, the pulley retainers preventing longitudinal movement of the pulleys towards each other.

5. The clamp applier as in claim 1 wherein the loop of cable is formed by securing a male member at one end of the cable into a female member at the other end of the cable.

6. The clamp applier as in claim 5 wherein the tube has a longitudinal opening sufficient to access the cable and to secure the male member of the cable into the female member of the cable, thus forming the loop.

7. The clamp applier as in claim 1 wherein the conduit is aligned slightly off-center of the longitudinal axis of the clamp applier.

8. A surgical clamp applier having a proximal end and a distal end, the clamp applier comprising:

a handle;

a pulley system comprising a proximal pulley, a distal pulley, and a loop of cable wrapped therearound, the distal pulley having a plurality of pins extending laterally therefrom;

a tube which houses substantially the entire loop of cable, the tube having a proximal end and a distal end;

a connector to connect the pulley system and the tube to the handle;

a proximal pulley retainer secured between the proximal end of the tube and the proximal pulley;

a distal pulley retainer secured between the distal end of the tube and the distal pulley;

a pulley actuator at the proximal end of the clamp applier to actuate the pulley system;

a conduit extending substantially the entire length of the tube and secured substantially therein, the conduit having a distal end for releasably engaging a clamp;

a rod extending substantially the entire length of the handle and of the tube, and housed substantially therein, the rod passing through the conduit;

a button at the proximal end of the clamp applier for propelling the rod distally; and a dial at the proximal end of the clamp applier for rotating the conduit about its longitudinal axis and for propelling the conduit distally.

9. A surgical clamp applier assembly comprising:

a clamp applier comprising
 (a) a handle,
 (b) a pulley system comprising a distal pulley with a plurality of pins extending laterally therefrom,
 (c) a connector to connect the pulley system to the handle,
 (d) a pulley actuator at the proximal end of the clamp applier to actuate the pulley system,
 (e) a conduit extending substantially the entire length of the clamp applier and secured substantially therein, the conduit having a distal end with a key-like tip,
 (f) a rod extending substantially the entire length of the clamp applier and housed substantially therein, the rod passing through the conduit,
 (g) means at the proximal end of the clamp applier for propelling the rod distally and for retracting the rod proximally, and
 (h) means at the proximal end of the clamp applier for rotating the conduit about its longitudinal axis and for propelling the conduit distally; and a surgical clamp comprising
 (a) a first jaw with a proximal end and a distal end, the first jaw having a keyhole at its proximal end adapted to receive the key-like tip of the conduit,
 (b) a second jaw with a proximal end and a distal end, the proximal end of the first jaw being connected to the proximal end of the second jaw at a joint, the second jaw having a plurality of pulley-pin holes at its proximal end adapted to receive the plurality of pins from the distal pulley, the second jaw being moveable relative to the first jaw from a substantially closed position to successive open positions,
 (c) a jaw-locking mechanism housed substantially within the joint, naturally biased in a locking position and predisposed to convert to an unlocking position when properly contacted by the rod.

10. The surgical clamp applier assembly as in claim 9 wherein the plurality of pins are inserted into the corresponding plurality of pulley-pin holes to engage the clamp with the clamp applier.

11. The surgical clamp applier assembly as in claim 10 wherein the key-like tip of the conduit is inside the keyhole and rotated sufficiently to substantially lock the clamp onto the clamp applier.

12. The surgical clamp applier assembly as in claim 11 wherein the jaw-locking mechanism is a leaf spring positioned distally relative to the keyhole, and wherein the leaf spring converts to an unlocking position when the means for propelling the rod distally is triggered such that the rod contacts and buckles the leaf spring.

13. A method of applying a detachable clamp with opposing jaws to a target vessel in an operating area, using a clamp applier with a proximal end and a distal end, comprising the steps of:

locking the clamp onto the distal end of the clamp applier by manipulating a dial at the proximal end of the clamp applier;

placing the opposing jaws of the clamp around opposing outer surfaces of the target vessel;

adjusting from the proximal end of the clamp applier the position of the jaws relative to each other to a desired position such that the target vessel is occluded at least partially;

unlocking the clamp from the clamp applier by manipulating the dial at the proximal end of the clamp applier; and removing the clamp applier from the clamp.

14. The method of applying a detachable clamp as in claim 13 wherein the adjusting step further comprises the steps of manipulating a button at the proximal end of the clamp applier to set the jaws in an unlocked position, and while maintaining the jaws in the unlocked position manipulating from the proximal end of the clamp applier an actuator to actuate a pulley system coupled to the jaws.

15. The method of applying a detachable clamp as in claim 13 wherein the locking step further comprises the steps of inserting pins from a distal pulley coupled to the clamp applier into pulley-pin holes in the clamp, and wherein the manipulation of the dial in the locking step further comprises the steps of rotating the dial partially about a longitudinal axis of the clamp applier and sliding the dial distally.

16. The method of applying a detachable clamp as in claim 13 wherein the manipulation of the dial in the unlocking step further comprises the steps of rotating the dial partially about a longitudinal axis of the clamp applier and sliding the dial proximally.

17. A method of clamping cardiac tissue during cardiovascular surgery comprising the steps of:

attaching a first clamp to a clamp applier;

using the clamp applier to clamp a major artery with the first clamp;

detaching the first clamp from the clamp applier;

attaching a second clamp to the clamp applier;

using the clamp applier to clamp a major vein with the second clamp; and detaching the second clamp from the clamp applier.

18. The method of clamping cardiac tissue as in claim 17 wherein the major artery is the aorta and wherein the first clamp has substantially straight opposing jaws.

19. The method of clamping cardiac tissue as in claim 17 wherein the major vein is one of the vena cavae and wherein the second clamp has substantially C-shaped jaws which form an annular configuration when in a closed position to seal the lumen of the major vein about the exterior of a cannula.

* * * * *